(12) United States Patent
Bednarski et al.

(10) Patent No.: US 8,530,681 B2
(45) Date of Patent: Sep. 10, 2013

(54) PHARMACEUTICAL COMPOSITIONS OF O-NITRO COMPOUNDS

(75) Inventors: Mark D. Bednarski, Los Altos, CA (US); Lynn M. Oehler, legal representative, Los Altos, CA (US); Susan Knox, Stanford, CA (US); Louis F. Cannizzo, Ogden, UT (US); Kirstin F. Warner, King George, VA (US); Robert B. Wardle, Ogden, UT (US); Stephen P. Velarde, Christiansburg, VA (US); Shoucheng Ning, Palo Alto, CA (US)

(73) Assignee: Alliant Techsystems Inc., Arlington, VA (US)

( * ) Notice: Subject to any disclaimer, the term of this patent is extended or adjusted under 35 U.S.C. 154(b) by 0 days.

(21) Appl. No.: 13/484,138

(22) Filed: May 30, 2012

(65) Prior Publication Data
US 2012/0237615 A1 Sep. 20, 2012

Related U.S. Application Data

(62) Division of application No. 11/502,974, filed on Aug. 11, 2006, now abandoned.

(60) Provisional application No. 60/707,896, filed on Aug. 12, 2005.

(51) Int. Cl.
*C07D 303/00* (2006.01)
*C07D 331/02* (2006.01)
*A61K 33/24* (2006.01)

(52) U.S. Cl.
USPC ............... 549/512; 549/1; 549/546; 424/617; 424/649

(58) Field of Classification Search
USPC .............................. 549/512, 1; 424/617, 649
See application file for complete search history.

(56) References Cited

U.S. PATENT DOCUMENTS

| | | | |
|---|---|---|---|
| 119,672 A | 10/1871 | Edward et al. | |
| 171,384 A | 12/1875 | Jenkins et al. | |
| 233,785 A | 10/1880 | Massey et al. | |
| 460,439 A | 9/1891 | Hildeeth | |
| 700,750 A | 5/1902 | Dougherty | |
| 2,978,453 A | 4/1961 | Milton | |
| 3,845,770 A | 11/1974 | Higuchi | |
| 3,916,899 A | 11/1975 | Theeuwes et al. | |
| 4,765,539 A | 8/1988 | Noakes et al. | |
| 5,112,598 A | 5/1992 | Biesalski et al. | |
| 5,336,784 A | 8/1994 | Hiskey et al. | |
| 5,521,203 A | 5/1996 | Adams et al. | |
| 5,556,611 A | 9/1996 | Biesalski et al. | |
| 5,579,458 A | 11/1996 | Yokosuka et al. | |
| 5,580,988 A | 12/1996 | Dave et al. | |
| 5,693,794 A | 12/1997 | Nielsen et al. | |
| 5,698,155 A | 12/1997 | Grosswald et al. | |
| 5,950,619 A | 9/1999 | van der Linden et al. | |
| 5,954,047 A | 9/1999 | Armer et al. | |
| 5,970,974 A | 10/1999 | Van Der Linden et al. | |
| 6,056,966 A * | 5/2000 | Selim et al. | 424/401 |
| 6,133,320 A | 10/2000 | Yallampalli et al. | |
| 6,245,799 B1 | 6/2001 | Asselin et al. | |
| 6,407,236 B1 | 6/2002 | Baraldi et al. | |
| 7,163,958 B2 | 1/2007 | Earl et al. | |
| 7,507,842 B2 | 3/2009 | Bednarski et al. | |
| 7,745,643 B2 | 6/2010 | Cannizzo et al. | |
| 2002/0137770 A1 | 9/2002 | Nara et al. | |
| 2004/0024057 A1 | 2/2004 | Earl et al. | |
| 2004/0138481 A1 | 7/2004 | Highsmith | |
| 2004/0167212 A1 | 8/2004 | Bednarski et al. | |
| 2005/0137191 A1 | 6/2005 | Thatcher et al. | |
| 2006/0111272 A1 | 5/2006 | Roberts et al. | |
| 2008/0255149 A1 | 10/2008 | Dobler et al. | |
| 2009/0093644 A1 | 4/2009 | Cannizzo et al. | |
| 2009/0163466 A1 | 6/2009 | Bednarski et al. | |
| 2011/0130572 A1 | 6/2011 | Cannizzo et al. | |
| 2012/0149678 A1 | 6/2012 | Oronsky et al. | |

FOREIGN PATENT DOCUMENTS

| | | |
|---|---|---|
| DE | 10111049 | 9/2002 |
| EP | 0412211 | 2/1991 |
| EP | 1336602 | 8/2003 |
| JP | A-60-116642 | 6/1985 |
| WO | WO95/32715 | 12/1995 |
| WO | WO98/16485 | 4/1998 |
| WO | WO99/16436 | 4/1999 |
| WO | WO99/59575 | 11/1999 |
| WO | WO00/06143 | 2/2000 |
| WO | WO01/77100 | 10/2001 |
| WO | WO 2004/032864 | 4/2004 |
| WO | WO2004/098538 | 11/2004 |
| WO | WO2004/113281 | 12/2004 |
| WO | WO2005/046661 | 5/2005 |
| WO | WO2007/022121 | 2/2007 |
| WO | WO2007/022225 | 2/2007 |

OTHER PUBLICATIONS

Needleman et al. (The J of Pharmacology and Exptl. Therapeutics, 165, 2, 1969, 286-88).*
Oxley, J. et al., Thermal Decomposition Pathways of 1,3,3-Trinitroazetidine (TNAZ), Related 3,3-Dinitroazetidium Salts, and 15N, 13C, and 2H Isotopomers, Journal of Physical Chemistry A, 1997, vol. 101, No. 24, p. 4375-4383.
Padwa, A. et al., Diastereofacial selectivity in azomethine ylide cycloaddition reactions derived from chiral x-cyanoaminosilanes, Tetrahedron, 1985, vol. 41, No. 17, p. 3529-35.
PCT International Search Report for International Application PCT/US2006/031917, Publication WO/2007/022225, dated Jul. 20, 2007.
PCT International Search Report for International Application PCT/US2006/031722, Publication WO/2007/022121, dated May 29, 2007.

(Continued)

*Primary Examiner* — Sreeni Padmanabhan
*Assistant Examiner* — Uma Ramachandran
(74) *Attorney, Agent, or Firm* — TraskBritt

(57) ABSTRACT

The present invention provides O-nitro compounds, pharmaceutical compositions of O-nitro compounds and methods of using O-nitro compounds and/or pharmaceutical compositions thereof to treat or prevent diseases or disorders characterized by abnormal cell proliferation, such as cancer, inflammation, cardiovascular disease and autoimmune disease.

4 Claims, 6 Drawing Sheets

(56) References Cited

OTHER PUBLICATIONS

PCT International Search Report for PCT/US2011/021500, mailed May 3, 2011.
Peiris, S.M. et al., Structures of dinitroazetidine and three of its carbonyl derivatives, Journal of Chemical Crystallography, 2001, vol. 30, No. 10, p. 647-653.
Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.
Raleigh, R.D., Verschoyle, C., et al., "Pharmacokinetics of Isotretinoin (ISO) in Rats Following Oral Dosing or Aerosol Inhalation," British J. Cancer, vol. 80, Suppl. 2, 96, 1999, P269.
Remington, "The Science and Practice of Pharmacy," 19th Edition, vol. II, pp. 1495-1562, 1577-1614, and 1660-1692, Mack Publishing Company, Easton, PA, 1995.
Rupnow, Brent A, et al., p53 Mediates Apoptosis Induced by C-Myc Activation in Hypoxic or Gamma Irradiated Fibroblasts, Cell Death and Differentiation, 1998, pp. 141-147, vol. 7.
Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research, vol. 5, No. 4, pp. 739-745, Apr. 1999.
Nicolescu Adreian Et al. ,:organic nitrites and NO: inhibition of lipid peroxidation and radical reactions, Chemical Research in Toxicology, Feb. 2004, pp. 185-196, vol. 17, No. 2.
Sandler, G., "Clinical evaluation of propatylnitrate in angina pectoris," British Medical Journal, vol. 2, No. 5269 (Dec. 30, 1961), pp. 1741-1744.
Sauder, Christopher D., "A Preliminary Trial of the Programmable Implantable Medication System for Insulin Delivery," The New England Journal of Medicine, vol. 321, No. 9, pp. 574-579, Aug. 31, 1989.
Sausville, Edward A., et al., Contributions of Human Tumor Xenografts to Anticancer Development, Cancer Research, 2006, pp. 3351-3354, vol. 66, No. 7.
Sefton, Michael V., "Implantable Pumps," CRC Crit. Rev. Biomed. Eng., vol. 14, No. 3, pp. 201-237, 1987.
Shokeir, A.A., Squamous Cell Carcinoma of the Bladder: pathology, diagnosis and treatment, BJU International, pp. 216-220, vol. 93.
Simpson, R.L., et al., Characterization of TNAZ, UCRL-ID-119672, Dec. 14, 1994, Lawrence Livermore National Laboratory, 15 pages.
Smolen, Victor F., et al., eds., "Controlled Drug Bioavailability," vol. 1, Drug Product Design and Performance, Ch. 7, pp. 203-237, John Wiley & Sons, New York, NY, copyright 1984.
Smith, (Oral Squamous Cell Carcinoma, 2008, Merck Manual).
Stamler, J.S., et al., "Inhaled ethyl nitrite gas for persistent pulmonary hypertension in infants," The Lancet, Lancet Limited, vol. 360, No. 9350 (Dec. 21, 2002), p. 2077, Great Britain.
Stratford, Ian J., et al., Bioreductive Drugs into the Next Millennium, Anti-Cancer Drug Design, 1998 pp. 519-528, vol. 13.
Treat, Joseph, et al., "Liposome Encapsulated Doxorubicin Preliminary Results of Phase I and Phase II Trials," Liposomes in the Therapy of Infectious Diseases and Cancer, Proceedings of the Ciba-Geigy-Squibb-UCLA Colloquium at Lake Tahoe, CA, Feb. 16-20, 1988, pp. 353-365.
Verma, R.K., et al., "Osmotically Controlled Oral Drug Delivery," Drug Dev. Ind. Pharm., vol. 26, No. 7, 2000, pp. 695-708.
Watt, Duncan S., et al., Evaluation of 1,3,3-Trinitrozaetidine (TNAZ)—A High Performance Melt-Castable Explosive, Weapons Systems Division Aeronautical and Maritime Research Laboratory, Report No. DSTO-TR-1000, issue date Jul. 2000, 34 pages.
Watt, Duncan S., et al., TNAZ Based Melt-Cast Explosives: Technology Review and AMRL Research Directions, Weapons Systems Division Aeronautical and Maritime Research Laboratory, Report DSTO-TR-0702, issue date Jul. 1987, 37 pages.
Wilson, William R., et al., Radiation-Activated Prodrugs as Hypoxia-Selective Cytotoxins: Model Studies with Nitroarylmethyl Quaternary Salts, Anti-Cancer Drug Design, 1998, pp. 663-685, vol. 13.
West, Anthony R., Solid State Chemistry and its Applications, 1988, pp. 358, and 365, Wiley, New York.
Written Opinion of the International Searching Authority for PCT/US2011/021500, mailed May 3, 2011.
Written Opinion of the International Searching Authority for PCT/US06/31722 mailed May 29, 2007.
Written Opinion of the International Searching Authority for PCT/US06/31917 mailed Jul. 20, 2007.
Xu et al., The Role of Nitric Oxide in Cancer, (Cell Research, 2002, pp. 311-320).
Yamaguchi, A., et al., Photodynamic Therapy with Motexafin Lutetium (Lu-Tex) Reduces Experimental Graft Coronary Artery Disease, Transplantation, Jun. 15, 2001, pp. 1526-1532, Vol. 71, No. 11 (abstract).
Yarmukhamedov, N.N. et al., One-step synthesis of substituted 3,3-dinitropiperidines and 1, 5-dinitro-3, 7diazabicyclo [3.3.1] nonanes from 1,3-dinitropropanes, Russian Chemical Bulletin, 2005, vol. 54, No. 2, p. 414-420.
Yen, Tzu-Chen, et al., F-FDG Uptake in Squamous Cell Carcinoma of the Cervix is Correlated with Glucose Transporter 1 Expression, The Journal of Nuclear Medicine, Jan. 2004, pp. 22-29, vol. 45, No. 1.
Zhang et al, Caplus an 1998:460439.
Zimmerman et al., "Pharmacological comparison of the steroisomers of glyceryl-1-nitrate," Arzneimittel-Forschung, 1994, pp. 474-477, Vo. 44, No. 4.
Eremenko, L.T. et al., "Synthesis of tetranitrates of conduritol-E and .alpah.-epoxy conduritol-E," Chemical Abstracts Service, retrieved from STN database accession No. 73:66844.
Akhavan, Jacqueline, Explosives and Propellants, Kirk-Othmer Encyclopedia of Chemical Technology, Sep. 17, 2004, pp. 719-744.
Alderman, D.A., "A Review of Cellulose Ethers in Hydrophilic Matrices for Oral Controlled-Release Dosage Forms," Int. J. Pharm. Tech. & Prod. Mfr., vol. 5, No. 3, pp. 1-9, 1984.
Armstrong, JS, et al., Role of Glutathione Depletion and Reactive Oxygen Species Generation in Apoptotic Signaling in a Human B Lymphoma Cell Line, Cell Death and Differentiation, 2002, pp. 252-263, vol. 9, Nature Publishing Group.
Ansari, Nabi G., et al., Primary squamous cell carcinoma of the prostate: a rare clinicopatholigical entity. Report of 2 cases and review of literature, Urol. Int., 2001, pp. 216-219, vol. 66, No. 4 (abstract).
Archibald, T.G., et al., "Synthesis and X-ray Crystal Structure of 1,3,3-Trinitroazetidine," J. Org. Chem, vol. 55, 1990, pp. 2920-2924.
Bamba, Morifere, et al., "Release Mechanisms in Gelforming Sustained Release Preparations," Int. J. Pharm., vol. 2, 1979, pp. 307-315.
Berge, Stephen M., et al., Pharmaceutical Salts, Journal of Pharmaceutical Sciences, Jan. 1977, pp. 1-19, vol. 66, No. 1.
Berman (Squamous Cell Carinoma, 2011, NLM, NIH document).
Brown, J. Martin, et al., Tirapazamine: Laboratory Data Relevant to Clinical Activity, Anti-Cancer Drug Design, 1998, pp. 529-539, vol. 13.
Kaplan D. L. et al. "Bi Defrasation of glycidol and glycidyl nitrate," Applied and Environmental Microbiology, 1982, pp. 144-150, vol. 43, No. 1.
Cecil Textbook of Medicine, 2000.
Chawla, Garima, et al., "Challenges in Polymorphism of Pharmaceuticals," CRIPS, vol. 5, No. 1, Jan.-Mar. 2004, pp. 9-12.
Crowder et al., Caplus an 1999: 171384.
Dave, Paritosh R., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., vol. 61, 1996, pp. 5453-5455.
Dermer (Bio/Technology, 1994, 12:320).
During, Matthew J., et al., "Controlled Release of Dopamine from a Polymeric Brain Implant: In Vivo Characterization," Annals of Neurology, vol. 25, No. 4, Apr. 1989, pp. 351-356.
Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.

Feuer, H. et al., The Mannich reaction of certain dinitro alcohols with glycine and ethanolamine, Journal of American Chemical Society, 1954, vol. 76, 5124-6.

Freshney (Culture of Animal Cells, A Manual of Basic Technique, Alan R. Liss, Inc., 1983, New York., p. 4).

Goodson, J. Max, "Dental Applications," Chapter 6 of Medical Applications of Controlled Release, vol. II, pp. 115-138, CRC Press, Inc., Boca Raton, FL, copyright 1984.

Granelli, Paola, SEL1L and Squamous Cell Carcinoma of the Esophagus, Clinical Cancer Research, Sep. 1, 2004, pp. 5857-5861, vol. 10.

Gura (Science, v278, 1997, pp. 1041-1042).

Hockel, Michael, et al., Tumor Hypoxia: Definitions and Current Clinical, Biologic, and Molecular Aspects, Journal of the National Cancer Institute, Feb. 21, 2001, pp. 266-276, vol. 93, No. 4.

Howard, Matthew A., III, et al., "Intracerebral Drug Delivery in Rats with Lesion-Induced Memory Deficits," J. Neurosurg., vol. 71, pp. 105-112, 1989.

Hiskey, Michael A., et al., Preparation of 1-Substituted-3,3-Dinitroazetidines, Journal of Energetic Materials, 1999, pp. 233-254, vol. 17, Dowden, Brodman & Devine, Inc.

Hiskey et al., caplus an 1993:233785.

Hiskey et al., caplus an 1994:700750.

Huguenin, Sandra, et al., "Evaluation of the antitumoral potential of different nitric oxide-donating non-steroidal anti-inflammatory drugs (NO-NSAIDs) on human urological tumor cell lines," Cancer Letters, vol. 218, 2005, pp. 163-170.

Ignarro, Louis J., Nitric Oxide Biology and Pathology, 2000, pp. 5, 895, and 908 Academic Press.

Jia, Q., et al., "NO donors with anticancer activity," Expert Opinion on Therapeutic Patents, vol. 12, No. 6 (2002), pp. 819-826, Great Britain.

Johnson, J.. et al., Relationships Between Drug Activity in NCI Preclinical in Vitro and in Vivo Models and Early Clinical Trials, British Journal of Cancer, 2001, pp. 1424-1431, vol. 84, No. 10.

Kashfi, Khosrow, et al., Nitric Oxide-Donating Nonsteroidal Anti-Inflammatory Drugs Inhibit the Growth of Various Cultured Human Cancel Cells: Evidence of a Tissue Type-Independent Effect, The Journal of Pharmacology and Experimental Therapeutics, 2002, pp. 1273-1282, vol. 303, No. 3.

Konovalova, N.P., et al., "Nitric oxide donor increases the efficiency of cytostatic therapy and retards the development of drug resistance," Nitric Oxide, vol. 8, No. 1 (Feb. 2003), pp. 59-64.

Kornblum et al., "Oxidative Substitution of Nitroparaffin Salts," J. Org. Chem., 1983, vol. 48, pp. 332-337.

Langer, Robert S., et al., eds., "Medical Applications of Controlled Release," vol. 1, Classes of Systems, Ch. 2, pp. 42-67, CRC Press, Inc., Boca Raton, FL, copyright 1984.

Langer, Robert, "New Methods of Drug Delivery," Science, New Series, vol. 249, No. 4976, Sep. 28, 1990, pp. 1527-1533.

Langer, Robert, et al., "Chemical and Physical Structure of Polymers as Carriers for Controlled Release of Bioactive Agents: A Review," JMS-Rev. Macromol. Chem. Phys., Ch. 23, pp. 61-126, 1983.

Levy, Robert J., "Inhibition of Calcification of Bioprosthetic Heart Valves by Local Controlled-Release Diphosphonate," Science, New Series, vol. 228, No. 4696, Apr. 12, 1985, pp. 190-192.

Ling, C., et al., "Phase I study of CM-Na combined with concurrent radiochemotherapy for advanced esophageal carcinoma (abstract)," Chinese Journal of Cancer, vol. 24, No. 5 (May 2005), (U.S. National Library of Medicine, Bethesda, MD, May 2005).

Lopez-Ferrer, Anna, et al., Differences in the O-Glycosylation Patterns Between Lung Squamous Cell Carcinoma and Adenocarcinoma, Am. J. Clin. Pathol., 2002, pp. 749-755, vol. 118, American Society for Clinical Pathology.

Marchand,A.P. et al, Additions of X-Y Across the C(3)-N o-Bond in I-Aza-3-ethylbicyclo(1.1.0) butane, Novel Routers to 3-Substituted Azetidines, Journal of Organic Chemistry, 1994, vol. 59, No. 18, p. 5499-5501.

Maxwell, P.H., et al., Hypoxia-inducible factor-1 modulates gene expression in solid tumors and influences both angiogenesis and tumor growth, Proc. Natl. Acad. Sci. USA, Jul. 1997, pp. 8104-8109, vol. 94, Medical Sciences.

Mendenhall, William M., et al., Radiation Therapy for Squamous Cell Carcinoma of the Tonsillar Region: A Preferred Alternative to Surgery?, Journal of Clinical Oncology, Jun. 2000, pp. 2219-2225, vol. 18, No. 11.

Morales-Suarez-Varela, Maria M., et al., Impact of Nitrates in Drinking Water on Cancel Mortality in Valencia, Spain, European Journal of Epidemiology, 1995, pp. 15-21, vol. 11.

Muehlstaedt et al., caplus an 1976:89768.

Nabi et al. in Urol. Int. (2001) vol. 66, pp. 216-219 (Abstract only).

Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., vol. 46, 2003, pp. 995-1004.

Ning, Shoucheng, et al., The Antiangiogenic Agents SU5416 and SU6668 Increase the Antitumor Effects of Fractionated Irradiation, Radiation Research, 2002, pp. 45-51, vol. 157.

Newman, Ann W., et al., "Solid-state analysis of the active pharmaceutical ingredient in drug products," DDT, vol. 8, No. 19, Oct. 2003, pp. 898-905.

Nitrates and Nitrites Answers to Frequently Asked Questions, Ohio Bureau of Environmental Health, Health Assessment Section, Nov. 1, 2006, 2 pages.

Garver, L, et al., "Catalyzed Oxidative Nitration of Nitronate Salts," J. Org. Chem., 1985, Vol. 50, pp. 1699-1702, © American Chemical Society.

Katritzky, A. et al., "Novel Syntheses of 1,3,3-Trinitroazetidine," J. Heterocyclic Chem., 1994, vol. 31, 271, 1994, pp. 271-275.

Marchand, A. et al., "A Novel Approach to the Synthesis of 1,3,3-Trinitroazetidine," J. Org. Chem., 1995, vol. 60 pp. 4943-4946, © American Chemical Society.

Straessler, N., et al., "Development of a Safe and Efficient Two-Step Synthesis for Preparing 1-Bromoacety1-3,3-dinitroazetidine, a Novel Clinical Anticancer Candidate," Org. Process Res. Dev., 2012, vol. 16, pp. 512-517, © American Chemical Society.

Crowder et al., Vibrational Analysis of High-energy Compounds: 1,3,3,-trinitroazetidine and 1-acetyl-3, 3-dinitroazetidine, Journal of Energetic Materials (1999) vol. 17, pp. 49-68.

International Search Report for PCT/US2011/064178 mailed Apr. 17, 2012, 4 pages.

International Written Opinion for PCT/US2011/064178 mailed Apr. 17, 2012, 4 pages.

International Search Report for PCT/US2012/038592 mailed Aug. 10, 2012, 5 pages.

International Written Opinion for PCT/US2011/038592 mailed Aug. 10, 2012, 5 pages.

International Search Report for PCT/US2011/021500 mailed Mar. 5, 2011, 4 pages.

Cai, T.B. et al., Expert Opinion on Therapeutic Patents, 2004, vol. 14, No. 6, p. 849-857 (Abstract Only).

Cook T. et al., Cancer Research, 2004, vol. 64, No. 21, p. 8015-21.

* cited by examiner

PHARMACEUTICAL COMPOSITIONS OF O-NITRO COMPOUNDS

CROSS-REFERENCE TO RELATED APPLICATIONS

This application is a divisional of U.S. patent application Ser. No. 11/502,974, filed Aug. 11, 2006, now abandoned, which application claims priority to U.S. Provisional Application Ser. No. 60/707,896, filed Aug. 12, 2005, each of which is hereby incorporated herein by this reference in its entirety.

TECHNICAL FIELD

The present invention relates generally to pharmaceutical compositions of O-nitro compounds and methods of using 0-nitro compounds and pharmaceutical compositions thereof to treat or prevent diseases characterized by abnormal cell proliferation such as cancer.

BACKGROUND OF THE INVENTION

Abnormal cell proliferation is a characteristic symptom of cancer. Further, abnormal cell proliferation has been implicated in numerous other diseases (e.g., cardiovascular diseases, inflammatory diseases such as rheumatoid arthritis, diabetic retinopathy, etc.). Although many methods for treating or preventing aberrant cell proliferation have been developed, a significant problem with most existing therapies is selectively distinguishing between normal and abnormal cell proliferation.

Radiotherapy is one promising approach to selectively targeting abnormal cell proliferation. A number of different radiosensitizers have been described in the art and include thiols, nitroimidazoles and metal texaphyrin compounds (see, e.g., Rosenthal et al., *Clin. Cancer Res.,* 1999, 739). Significant problems with existing radiosensitization approaches are (1) the formation of toxic byproducts derived from the radiosensitizers, which has limited their usefulness in cancer therapy; and (2) achieving sufficiently high density of free radicals to be efficacious under dose-limiting toxicity.

Another popular approach to selectively targeting abnormal cell proliferation is treatment with bioreductive compounds, which are selectively activated in a reducing environment. Since many cancers typically contain regions of low oxygen tension (i.e., hypoxia), compounds with low redox potentials (i.e., bioreductive compounds) may be selectively activated in the reducing environment of tumor cells without external activation.

Accordingly, new compounds are required to fully explore treating or preventing abnormal cell proliferation. These new compounds may have radiotherapeutic activity or bioreductive activity. Such compounds may be effective in treating or preventing various diseases associated with abnormal cell proliferation such as cancer without forming toxic byproducts.

SUMMARY OF THE INVENTION

The present invention satisfies this and other needs by providing O-nitro compounds, pharmaceutical compositions of O-nitro compounds and methods of using O-nitro compounds or pharmaceutical compositions thereof to treat or prevent diseases associated with abnormal cell proliferation.

In a first aspect, the present invention provides methods for treating or preventing diseases or disorders characterized by abnormal cell proliferation. The methods generally involve administering to a patient in need of such treatment or prevention a therapeutically effective amount of an O-nitro compound or a pharmaceutically acceptable salt, hydrate, solvate or N-oxide thereof.

In a second aspect, the present invention provides pharmaceutical compositions of O-nitro compounds. The pharmaceutical compositions generally comprise one or more O-nitro compounds, pharmaceutically acceptable salts, hydrates, solvates or N-oxides thereof, and a pharmaceutically acceptable vehicle. The choice of vehicle will depend upon, among other factors, the desired mode of administration.

In a third aspect, the current invention provides pharmaceutical compositions for treating or preventing diseases or disorders characterized by abnormal cell proliferation. The methods generally involve administering to a patient in need of such treatment or prevention a therapeutically effective amount of a pharmaceutical composition comprising an O-nitro compound or a pharmaceutically acceptable salt, hydrate, solvate or N-oxide thereof and a pharmaceutically acceptable vehicle.

DETAILED DESCRIPTION OF THE INVENTION

Definitions

Figure 1:
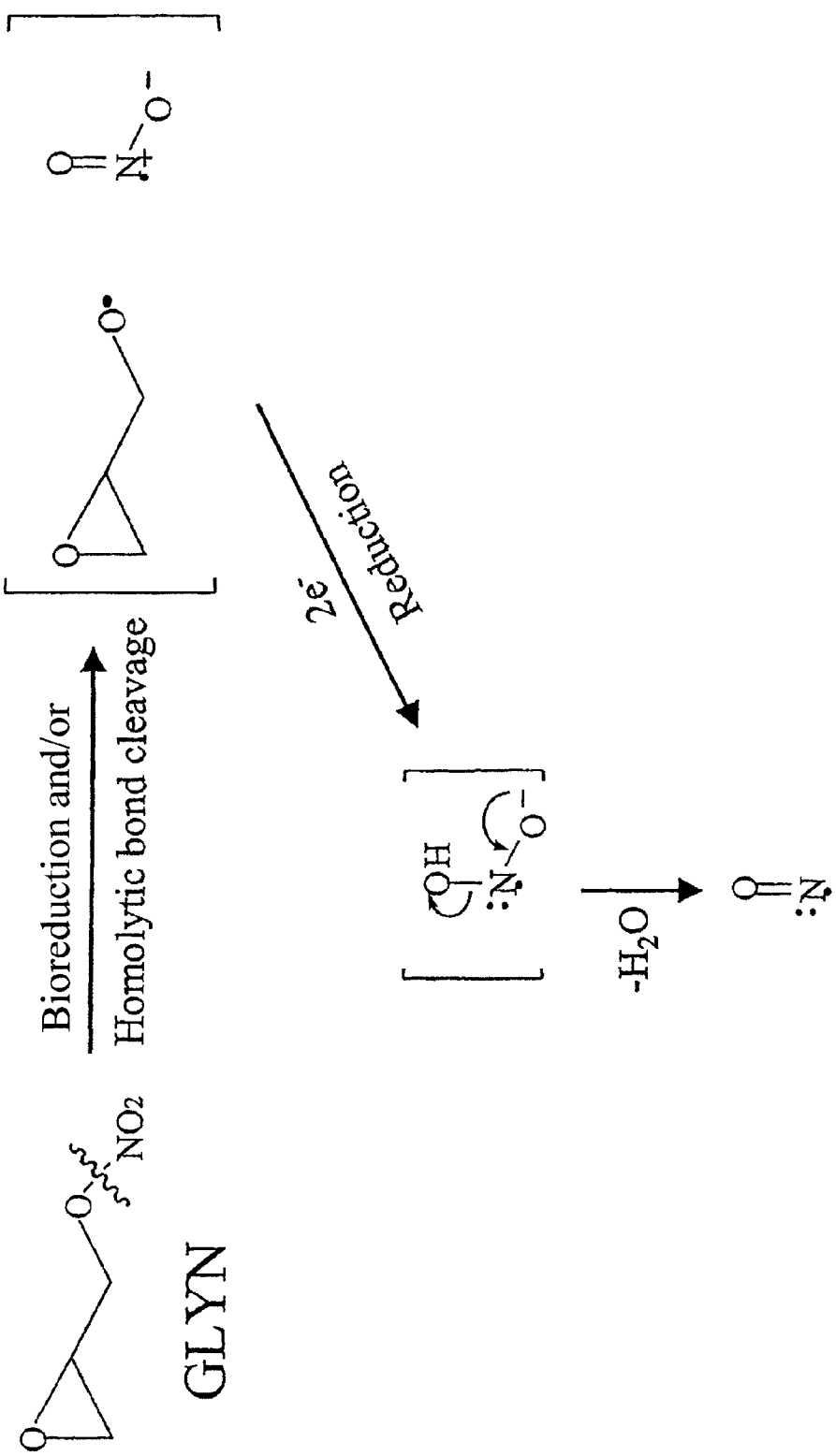
FIG. 1 illustrates a possible mechanism of chemosensitization for O—$NO_2$ compounds.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to: methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl, cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises 1 to 10 carbon atoms. In still other embodiments, an alkyl group comprises from 1 to 6 carbon atoms.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to: methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to: ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like.

"Alkynyl," by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to: ethynyl; propynyls such as prop-1-yn-1-yl, prop-2-yn-1-yl, etc.; butynyls such as but-1-yn-1-yl, but-1-yn-3-yl, but-3-yn-1-yl, etc., and the like.

"Adamantyl," by itself or as part of another substituent, refers to hydrocarbon radical derived by the removal of one hydrogen atom from a single carbon atom of adamantane.

"Cycloalkyl," by itself or as part of another substituent, refers to a saturated or unsaturated cyclic alkyl radical derived by the removal of one hydrogen atom from a single carbon atom. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group is ($C_3$-$C_{10}$) cycloalkyl. In other embodiments, the cycloalkyl group is ($C_3$-$C_7$) cycloalkyl.

"Cycloheteroalkyl," by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Fused cycloalkyl," by itself or as part of another substituent, refers to a saturated or unsaturated fused cyclic alkyl radical of the form m.n.0 alkyl, where m and n are integers greater than 1, derived by the removal of one hydrogen atom from a single carbon atom of a parent fused cycloalkyl compound. Typical fused cycloalkyl groups include, but are not limited to, 4.2.0 octane, 4.1.0 heptane, 3.2.0 heptane, 3.1.0 hexane. In some embodiments, the fused cycloalkyl group is ($C_3$-$C_{10}$) fused cycloalkyl.

"Fused cycloheteroalkyl," by itself or as part of another substituent, refers to a saturated or unsaturated fused cycloalkyl radical in which one or more carbon atoms (and any associated hydrogen atoms) are independently replaced with the same or different heteroatom. In some embodiments, the fused cycloheteroalkyl group is ($C_3$-$C_{10}$) fused cycloheteroalkyl.

"Cubyl," by itself or as part of another substituent, refers to hydrocarbon radical derived by the removal of one hydrogen atom from a single carbon atom of cubane.

"Heteroalkyl, heteroalkanyl, heteroalkenyl and heteroalkynyl," by themselves or as part of another substituent, refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups that can be included in these groups include, but are not limited to, —O—, —S—, —O—O—, —S—S—, —O—S—, —NR$^{34}$R$^{35}$—, =N—N=, —N=N—, —N=N—NR$^{36}$R$^{37}$, —PR$^{38}$—, —P(O)$_2$—, —POR$^{39}$—, —O—P(O)$_2$—, —SO—, —SO$_2$—, —SnR$^{40}$R$^{41}$— and the like, where R$^{34}$, R$^{35}$, R$^{36}$, R$^{37}$, R$^{38}$, R$^{39}$, R$^{40}$ and R$^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Pharmaceutically acceptable salt" refers to a salt of an O-nitro compound, which is pharmaceutically acceptable and possesses the desired pharmacological activity of the parent compound. Such salts: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like.

"Pharmaceutically acceptable vehicle" refers to a diluent, adjuvant, excipient or carrier with which an O-nitro compound is administered.

"Patient" includes humans and other mammals.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Substituted" refers to a group in which one or more hydrogen atoms are independently replaced with the same or different substituent(s). Typical substituents include, but are not limited to -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $-ONO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$, where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In some embodiments, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $-ONO_2$, $=N_2$, $-N_3$, $-S(O)_2R^{60}$, $-OS(O_2)O^-$, $-OS(O)_2R^{60}$, $-P(O)(O^-)_2$, $P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^{60}R^{61}$, where $R^{60}$, $R^{61}$ and $R^{62}$ are as defined above. In other embodiments, substituents include -M, $-R^{60}$, $=O$, $-OR^{60}$, $-SR^{60}$—$NR^{60}R^{61}$, $-CF_3$, $-CN$, $-NO_2$, $-ONO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$ and $-C(O)O^-$, where $R^{60}$, $R^{61}$ and $R^{62}$ are as defined above. In still other embodiments, substituents include -M, $-R^{60}$, $=O$, $-OR^{60}$, $-SR^{60}$, $-NR^{60}R^{61}$, $-CF_3$, $-CN$, $-NO_2$, $-ONO_2$, $-S(O)_2R^{60}$, $-OP(O)(OR^{60})(OR^{61})$, $-C(O)R^{60}$, $-C(O)OR^{60}$ and $-C(O)O^-$, where $R^{60}$, $R^{61}$ and $R^{62}$ are as defined above.

"Treating" or "treatment" of any disease or disorder refers, in some embodiments, to ameliorating the disease or disorder (i.e., arresting or reducing the development of the disease or at least one of the clinical symptoms thereof). In other embodiments, "treating" or "treatment" refers to ameliorating at least one physical parameter, which may not be discernible by the patient. In yet other embodiments "treating" or "treatment" refers to inhibiting the disease or disorder, either physically (e.g., stabilization or eradication of a discernible symptom), physiologically (e.g., stabilization or eradication of a physical parameter), or both. In still other embodiments, "treating" or "treatment" refers to delaying the onset of the disease or disorder.

"Therapeutically effective amount" means the amount of a compound that, when administered to a patient for treating or preventing a disease, is sufficient to effect such treatment or prevention of the disease. The "therapeutically effective amount" will vary depending on the compound, the disease and its severity, and the age, weight, etc., of the patient to be treated.

Reference will now be made in detail to embodiments of the invention. While the invention will be described in conjunction with these embodiments, it will be understood that it is not intended to limit the invention to those preferred embodiments. To the contrary, it is intended to cover alternatives, modifications, and equivalents as may be included within the scope of the invention as defined by the appended claims.

Methods of Using O-Nitro Compounds to Treat or Prevent Abnormal Cell Proliferation The present invention provides O-nitro compounds, pharmaceutical compositions of O-nitro compounds and methods of using O-nitro compounds or pharmaceutical compositions thereof to treat or prevent diseases associated with abnormal cell proliferation.

The methods generally involve administering to a patient in need of such treatment or prevention a therapeutically effective amount of an O-nitro compound or a pharmaceutically acceptable salt, hydrate, solvate or N-oxide thereof. In some embodiments, the O-nitro compound is intracellularly activated by the reducing environment of a tumor cell. In other embodiments, the patient is irradiated to activate the O-nitro compound. Accordingly, in some embodiments, the O-nitro compounds of the present invention may be activated by both intracellular reduction and external irradiation. In these embodiments, a synergistic or additive effect may be observed.

O-nitro compounds are generally organic compounds substituted with one or more O-nitro groups. Typically, O-nitro compounds have a high enthalapy of formation (i.e., decomposition of O-nitro compounds releases a high amount of energy). Preferably, O-nitro compounds have an enthalapy of formation that varies between about 5 kcal/mole and about 150 kcal/mole, more preferably, between about 10 kcal/mole and about 110 kcal/mole. The enthalapy of formation of O-nitro compounds may be readily calculated by methods known to the skilled artisan. Accordingly, O-nitro compounds include those O-nitro compounds that decompose with explosive force upon activation. Such compounds may be readily identified by those of skill in the art by calculation of the enthalapy of formation.

O-nitro compounds may also be reduced at low reduction potentials. Cyclic voltametry demonstrates that electron transfer to O-nitro compounds occurs between about −0.1 volt and about −1.0 volt using standard electrodes (e.g., mercury or carbon cathode and platinum anode) and electrolyte solutions.

O-nitro compounds may contain a high density of nitro groups (i.e., the nitro groups represent a significant fraction of the overall mass of the compound). In some embodiments, an O-nitro compound contains two nitro groups. In other embodiments, an O-nitro compound contains three nitro groups. In still other embodiments, an O-nitro compound contains six nitro groups.

In some embodiments, the O-nitro compound has a ratio of nitro groups to carbon atoms of 1:1. In other embodiments, the O-nitro compound has a ratio of nitro groups to carbon atoms of 1:2.

In some embodiments, the O-nitro compound has the structure $R^1$—O—$NO_2$ where $R^1$ is alkyl, substituted alkyl, cycloalkyl, substituted cycloalkyl, cycloheteroalkyl, substituted cycloheteroalkyl, heteroalkyl, substituted heteroalkyl, fused cycloalkyl, substituted fused cycloalkyl, fused cycloalkylcycloheteroalkyl, substituted fused cycloalkylcycloheteroalkyl, cubyl, substituted cubyl, adamantyl or substituted adamantyl.

In other embodiments, $R^1$—O—$NO_2$ has the structure:

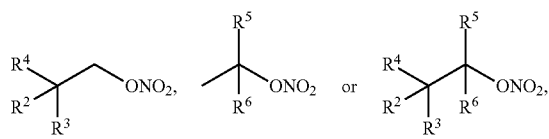

wherein $R^2$, $R^3$, $R^4$, $R^5$ and $R^6$ are independently hydrogen, alkyl or substituted alkyl.

In still other embodiments, $R^1$—O—$NO_2$ has the structure:

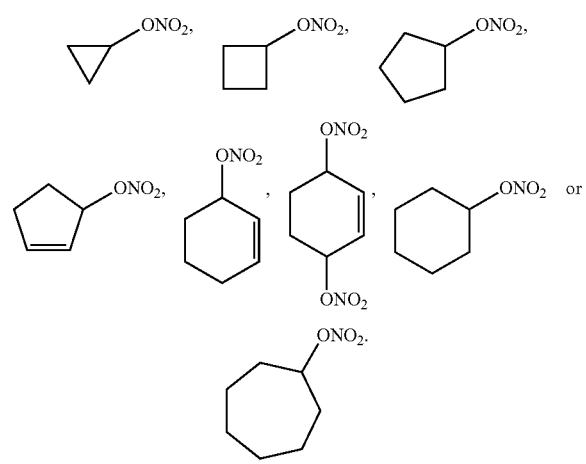

In still other embodiments, $R^1$—O—$NO_2$ has the structure:

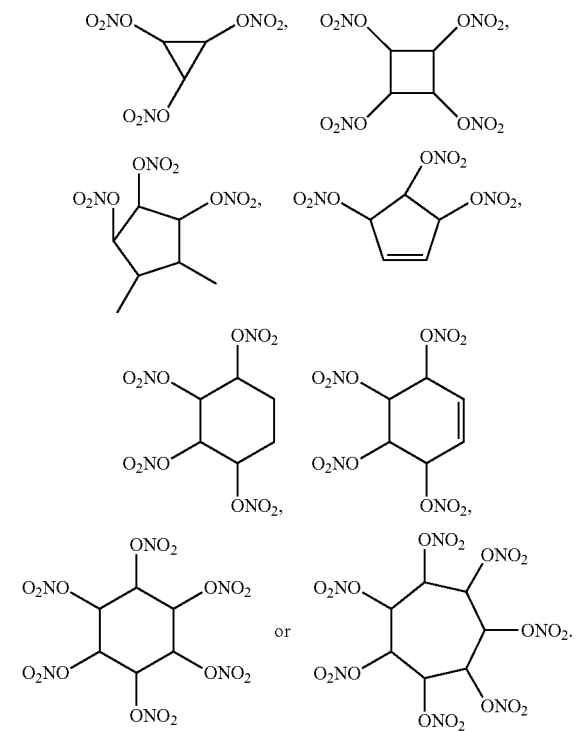

In still other embodiments, $R^1$—O—$NO_2$ has the structure:

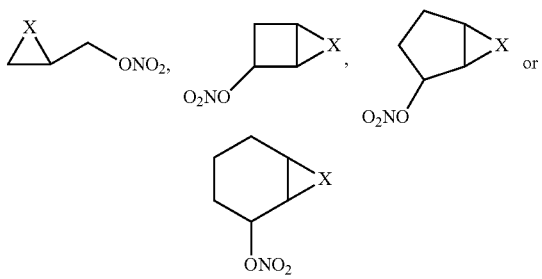

wherein X is —S—, —O—, —N($R^7$), —P(O)O$R^7$, or —B$R^7$ where $R^7$ is hydrogen or alkyl.

In still other embodiments, $R^1$—O—$NO_2$ has the structure:

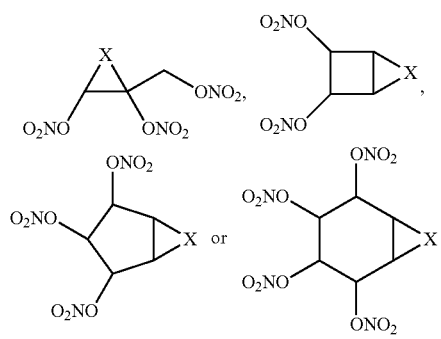

wherein X is —S—, —O—, —N($R^7$), —P(O)O$R^7$, or —B$R^7$ where $R^7$ is hydrogen or alkyl.

In still other embodiments, $R^1$—O—$NO_2$ has the structure:

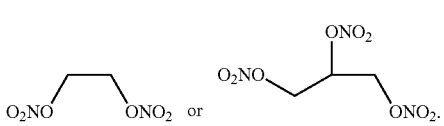

In still other embodiments, $R^1$—O—$NO_2$ has the structure:

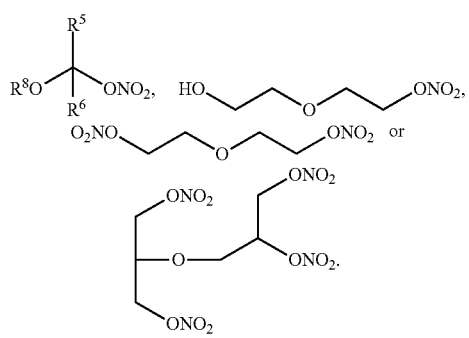

In still other embodiments, R¹—O—NO₂ has the structure:

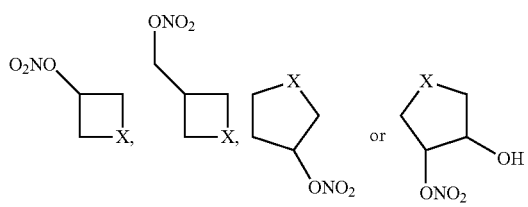

wherein X is —S—, —O— or —N(R⁷) where R⁷ is hydrogen or alkyl.

Nitrate esters including, but not limited to, diglycerol tetranitrate, 3-nitratomethyl oxetane, bis 3,3-nitrotomethyl oxetane, triethylene glycol dinitrate, trimethylol trinitrate, pentaerythritol tetranitrate, n-butyl-2-nitratomethyl nitramine and polyglycidyl nitrate can be to practice the instant invention.

O-nitro compounds may exist in several tautomeric forms and mixtures thereof. O-nitro compounds may also include isotopically labeled compounds where one or more atoms have an atomic mass different from the atomic mass conventionally found in nature. Examples of isotopes that may be incorporated into O-nitro compounds include, but are not limited to, $^2$H, $^3$H, $^{13}$C, $^{14}$C, $^{15}$N, $^{18}$O and $^{17}$O. O-nitro compounds may exist in unsolvated forms as well as solvated forms, including hydrated forms or N-oxides. In general, hydrated and solvated fowls are within the scope of the present invention. Certain O-nitro compounds may exist in multiple crystalline or amorphous forms. In general, all physical forms are equivalent for the uses contemplated by the present invention and are intended to be within the scope of the present invention.

O-nitro compounds may be activated by intracellular reduction. In some embodiments, O-nitro compounds are activated by intracellular reduction in hypoxic tumor cells, secondary to elevated glutathione levels (high GSH:GSSG (i.e., glutathione to glutathione disulfide ratios)) and possibly high levels of other antioxidant enzymes in many tumor cells and/or a median tumor cell pO₂ of less than about 10 mm Hg.

O-nitro compounds may also be activated by application of external energy. Methods useful for decomposing O-nitro compounds include, but are not limited to, irradiation (e.g., with x-rays, visible light, infrared irradiation), ultrasound (e.g., focused ultrasound), electrochemical reduction, heating, co-administration of free radical initiators (e.g., thiols), etc. In some embodiments, an O-nitro compound is activated by photon irradiation of the patient. In other embodiments, the patient's tumor is irradiated using a linear accelerator at a dose rate of about 100 cGy/min. In still other embodiments, the patient may also be treated with electron beam therapy, interoperative radiation therapy, stereostatic radiosurgery and high or low dose brachytherapy.

In still other embodiments, the entire patient may be irradiated. In still other embodiments, a portion of the patient is irradiated so that only the O-nitro compound localized in the irradiated portion (e.g., tumor region) of the patient is activated. Preferably, the portion of the patient that is irradiated is the site of abnormal cell proliferation.

Without wishing to be bound by theory, irradiation or reduction of O-nitro compounds may lead to formation of free radicals, such as the alkoxy radical, infra, that subsequently prevent cell replication and kill cells, presumably by interfering with DNA replication and/or reacting with cell membranes. However, other mechanisms may account for the efficacy of O-nitro compounds in treating or preventing abnormal cell proliferation. FIG. 1 illustrates a possible mechanism that may reflect why O-nitro compounds are effective in cancer therapy. Reduction and/or hemolytic cleavage of the O-nitro compound GLYN leads to an alkoxy radical and the NO₂ radical. The NO₂ radical decomposes via further reduction and loss of water to NO, which is well known to those of skill in the pharmaceutical arts as a potent vasodilating agent. NO may alter blood flow and permeability in pathological regions, which, in turn, can affect drug delivery. NO may also alter the degree of tissue oxygenation, which may alter the effect of radiation therapy.

O-nitro compounds may be obtained via conventional synthetic methods described in the art or are commercially available. Starting materials useful for preparing O-nitro compounds and intermediates thereof are commercially available or can be prepared by well-known synthetic methods. Other methods for synthesis of the O-nitro compounds described herein and/or starting materials are either described in the art or will be readily apparent to the skilled artisan.

In accordance with the invention, an O-nitro compound or a pharmaceutical composition thereof is administered to a patient, preferably a human, suffering from a disease characterized by abnormal cell proliferation. The O-nitro compound and pharmaceutical compositions thereof may be used to treat or prevent diseases characterized by abnormal cell proliferation.

Diseases characterized by abnormal cell proliferation include cancer (e.g., any vascularized tumor, solid tumors, including, but not limited to, carcinomas of the lung, breast, ovary, stomach, pancreas, larynx, esophagus, testes, liver, parotid, bilary tract, colon, rectum, cervix, uterus, endometrium, kidney, bladder, prostrate and thyroid, lymphohematopoietic malignancies, squamous cell carcinomas, adenocarcinomas, small cell carcinomas, melanomas, gliomas, neuroblastomas, sarcomas (e.g., angiosarcomas, chondrosarcomas), diabetes, cardiovascular diseases (e.g., arteriosclerosis), inflammatory diseases (e.g., arthritis, diabetic retinopathy, rheumatoid arthritis, neovascular glaucoma and psoriasis) and autoimmune diseases.

In other embodiments, O-nitro compounds may be used for in vitro sterilization. Biological solutions may be treated with O-nitro compounds, which are toxic to pathogenic bacteria, viruses and cells. This process can also be catalyzed by the application of external energy such as light and heat.

Further, in certain embodiments, an O-nitro compound and/or pharmaceutical compositions thereof are administered to a patient, preferably a human, as a preventative measure against various diseases or disorders characterized by abnormal cell proliferation. Thus, O-nitro compounds and/or pharmaceutical compositions thereof may be administered as a preventative measure to a patient having a predisposition for a disease characterized by abnormal cell proliferation. Accordingly, O-nitro compounds and/or pharmaceutical compositions thereof may be used for the prevention of one disease or disorder and concurrently treating another (e.g., preventing arthritis while treating cancer).

The suitability of O-nitro compounds and/or pharmaceutical compositions thereof in treating or preventing various diseases or disorders characterized by abnormal cell proliferation may be determined by methods described in the art.

Therapeutic/Prophylactic Administration

O-nitro compounds and/or pharmaceutical compositions thereof may be advantageously used in human medicine. As previously described, O-nitro compounds and/or pharmaceutical compositions thereof are useful for the treatment or prevention of various diseases or disorders.

When used to treat or prevent the above disease or disorders, O-nitro compounds and/or pharmaceutical compositions thereof may be administered or applied singly, or in combination with other agents. O-nitro compounds and/or pharmaceutical compositions thereof may also be administered or applied singly or in combination with other pharmaceutically active agents (e.g., other anti-cancer agents), including other O-nitro compounds and/or pharmaceutical compositions thereof.

The current invention provides methods of treatment and prophylaxis by administration to a patient of a therapeutically effective amount of an O-nitro compound and/or pharmaceutical composition thereof The patient is preferably a mammal and, most preferably, is a human.

O-nitro compounds and/or pharmaceutical compositions thereof may be administered orally. O-nitro compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known (e.g., encapsulation in liposomes, microparticles, microcapsules, capsules, etc.) that can be used to administer an O-nitro compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin. The preferred mode of administration is left to the discretion of the practitioner and will depend in part upon the site of the medical condition. In most instances, administration will result in the release of O-nitro compounds and/or pharmaceutical compositions thereof into the bloodstream.

In specific embodiments, it may be desirable to administer one or more O-nitro compounds and/or pharmaceutical compositions thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes or fibers. In some embodiments, administration can be by direct injection at the site (or former site) of the disease or disorder.

In certain embodiments, it may be desirable to introduce one or more O-nitro compounds and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

O-nitro compounds and/or pharmaceutical compositions thereof may also be administered directly to the lung by inhalation. For administration by inhalation, O-nitro compounds and/or pharmaceutical compositions thereof may be conveniently delivered to the lung by a number of different devices. For example, a Metered Dose Inhaler ("MDI"), which utilizes canisters that contain a suitable low boiling propellant (e.g., dichlorodifluoromethane, trichlorofluoromethane, dichlorotetrafluoroethane, carbon dioxide or any other suitable gas) may be used to deliver O-nitro compounds and/or pharmaceutical compositions thereof directly to the lung.

Alternatively, a Dry Powder Inhaler ("DPI") device may be used to administer an O-nitro compound and/or pharmaceutical composition thereof to the lung. DPI devices typically use a mechanism such as a burst of gas to create a cloud of dry powder inside a container, which may then be inhaled by the patient and are well known in the art. A popular variation is the multiple dose DPI ("MDDPI") system, which allows for the delivery of more than one therapeutic dose. MDDPI devices are commercially available from a number of pharmaceutical companies (e.g., Schering Plough, Madison, N.J.). For example, capsules and cartridges of gelatin for use in an inhaler or insufflator may be formulated containing a powder mix of an O-nitro compound and/or pharmaceutical composition thereof and a suitable powder base such as lactose or starch for these systems.

Another type of device that may be used to deliver an O-nitro compound and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer is used to deliver an O-nitro compound and/or pharmaceutical composition thereof to the lung. Nebulizers create aerosols from liquid drug formulations by using, for example, ultrasonic energy to form fine particles that may be readily inhaled (see, e.g., Raleigh et al., *British J. Cancer,* 1999, 80, Suppl. 2, 96). Examples of nebulizers include devices supplied by Sheffield Pharmaceuticals, St. Louis, Mo. (Armer et al., U.S. Pat. No. 5,954,047; van der Linden et al., U.S. Pat. No. 5,950,619; van der Linden et al., U.S. Pat. No. 5,970,974), and Batelle Pulmonary Therapeutics, Columbus, Ohio.

In some embodiments, an electrohydrodynamic ("EHD") aerosol device is used to deliver an O-nitro compound and/or pharmaceutical composition thereof to the lung of a patient. EHD aerosol devices use electrical energy to aerosolize liquid drug solutions or suspensions (see, e.g., Noakes et al., U.S. Pat. No. 4,765,539). The electrochemical properties of the formulation may be important parameters to optimize when delivering an O-nitro compound and/or pharmaceutical composition thereof to the lung with an EHD aerosol device and such optimization is routinely performed by one of skill in the art. EHD aerosol devices may more efficiently deliver drugs to the lung than existing pulmonary delivery technologies.

In other embodiments, an O-nitro compound and/or pharmaceutical composition thereof can be delivered in a vesicle, in particular, a liposome (e.g., Langer, 1990, *Science* 249: 1527-1533; Treat et al., in "Liposomes in the Therapy of Infectious Disease and Cancer," Lopez-Berestein and Fidler (eds.), Liss, New York, pp. 353-365 (1989)).

In still other embodiments, an O-nitro compound and/or pharmaceutical composition thereof can be delivered via sustained release systems, preferably oral sustained release systems. In some embodiments, a pump may be used (e.g., Langer, supra, Sefton, 1987, *CRC Crit. Ref Biomed. Eng.* 14:201; Saudek et al., 1989, *N. Engl. J. Med.* 321:574).

In still other embodiments, polymeric materials can be used (e.g., "Medical Applications of Controlled Release," Langer and Wise (eds.), CRC Press, Boca Raton, Fla. (1974); "Controlled Drug Bioavailability," *Drug Product Design and Performance*, Smolen and Ball (eds.), Wiley, New York (1984); Langer et al., 1983, *J. Macromol. Sci. Rev. Macromol. Chem.* 23:61; Levy et al., 1985, *Science* 228:190; During et al., 1989, *Ann. Neurol.* 25:351; Howard et al., 1989, *J. Neurosurg.* 71:105).

In other embodiments, polymeric materials are used for oral sustained release delivery. Polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described in the art (Alderman, *Int. J. Pharm. Tech. & Prod. Mfr.* 1984, 5(3) 1-9). Factors affecting drug release are well known to the skilled artisan and have been described in the art (Bamba et al., *Int. J. Pharm.* 1979, 2:307).

In still other embodiments, enteric-coated preparations can be used for oral sustained release administration. Coating materials include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.,* 2000, 26:695-708). In other embodiments, OROS® osmotic devices are used for oral sustained release delivery devices (Theeuwes et al., U.S. Pat. No. 3,845,770; Theeuwes et al., U.S. Pat. No. 3,916,899).

In other embodiments, a controlled-release system can be placed in proximity of the target of the O-nitro compound and/or pharmaceutical composition, thus requiring only a fraction of the systemic dose (e.g., Goodson, in "Medical Applications of Controlled Release," supra, vol. 2, pp. 115-138 (1984)). Other controlled-release systems previously may also be used (Langer, 1990, *Science* 249:1527-1533).

Pharmaceutical Compositions

The present pharmaceutical compositions typically contain a therapeutically effective amount of one or more O-nitro compounds, preferably in purified form, together with a suitable amount of a pharmaceutically acceptable vehicle, so as to provide the form for proper administration to a patient. When administered to a patient, the O-nitro compound and pharmaceutically acceptable vehicles are preferably sterile. Water is a preferred vehicle when the O-nitro compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising an O-nitro compound may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate processing of compounds into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (e.g., Grosswald et al., U.S. Pat. No. 5,698,155). A general discussion of the preparation of pharmaceutical compositions may be found in Remington, "*The Science and Practice of Pharmacy,*" 19th Edition.

For topical administration, an O-nitro compound may be formulated as solutions, gels, ointments, creams, suspensions, etc., as is well known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, O-nitro compounds are formulated in accordance with routine procedures as a pharmaceutical composition adapted for intravenous administration to human beings. Typically, O-nitro compounds are solutions in sterile isotonic aqueous buffer for intravenous administration. For injection, O-nitro compounds may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water-free concentrate in a hermetically sealed container such as an ampoule or sachette indicating the quantity of active agent. When the O-nitro compounds are administered by infusion, it can be dispensed, for example, with an infusion bottle containing sterile pharmaceutical grade water or saline. When the O-nitro compound is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers between pH 4 and pH 6 (e.g., acetate, citrate, or ascorbate at between about 5.0 mM to about 50.0 mM), etc. Additionally, flavoring agents, preservatives, coloring agents, bile salts, acylcarnitines and the like may be added.

For buccal administration, the pharmaceutical compositions may take the form of tablets, lozenges, etc., formulated in a conventional manner.

Liquid drug formulations suitable for use with nebulizers and liquid spray devices and EHD aerosol devices typically include an 0-nitro compound with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds. This material may be a liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

An O-nitro compound may also be formulated in rectal or vaginal pharmaceutical compositions such as suppositories or retention enemas, e.g., containing conventional suppository bases such as cocoa butter or other glycerides.

In addition to the formulations described previously, an O-nitro compound may also be formulated as a depot preparation. Such long-acting formulations may be administered by implantation (for example, subcutaneously or intramuscularly) or by intramuscular injection. Thus, for example, an O-nitro compound may be formulated with suitable polymeric or hydrophobic materials (e.g., as an emulsion in an acceptable oil) or ion exchange resins, or as sparingly soluble derivatives, such as a sparingly soluble salt.

When an O-nitro compound is acidic or basic, it may be included in any of the above-described formulations as the free acid or free base, a pharmaceutically acceptable salt, a solvate or hydrate. Pharmaceutically acceptable salts substantially retain the activity of the free acid or base, may be prepared by reaction with bases or acids and tend to be more soluble in aqueous and other protic solvents than the corresponding free acid or base form.

Doses

An O-nitro compound and/or pharmaceutical composition thereof, will generally be used in an amount effective to achieve the intended purpose. For use in treating or preventing the above diseases or disorders, the O-nitro compound and/or pharmaceutical compositions thereof are administered or applied in a therapeutically effective amount.

The amount of an O-nitro compound and/or pharmaceutical composition thereof that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of an O-nitro compound and/or pharmaceutical composition thereof administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. Dosing may be repeated intermittently, may be provided alone or in combination with other drugs and may continue as long as required for effective treatment of the disease state or disorder.

Suitable dosage ranges for oral administration are dependent on the efficiency of radiosensitization, but are generally about 0.001 mg to about 100 mg of the O-nitro compound per kg body weight. Dosage ranges may be readily determined by methods known to the artisan of ordinary skill.

Suitable dosage ranges for intravenous (i.v.) administration are about 0.01 mg to about 100 mg per kg/body weight. Suitable dosage ranges for intranasal administration are generally about 0.01 mg/kg body weight to about 1 mg/kg body weight. Suppositories generally contain about 0.01 milligram to about 50 milligrams of an O-nitro compound per kg/body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kg/body weight. Effective doses may be extrapolated from dose-response curves derived from in vitro or animal model test systems. Such animal models and systems are well known in the art.

The O-nitro compounds may be assayed in vitro and in vivo, for the desired therapeutic or prophylactic activity, prior to use in humans. For example, in vitro assays can be used to determine whether administration of a specific O-nitro compound or a combination of O-nitro compounds is preferred. The O-nitro compound may also be demonstrated to be effective and safe using animal model systems.

Preferably, a therapeutically effective dose of an O-nitro compound and/or pharmaceutical composition thereof described herein will provide therapeutic benefit without causing substantial toxicity. Toxicity of O-nitro compounds and/or pharmaceutical compositions thereof may be determined using standard pharmaceutical procedures and may be readily ascertained by the skilled artisan. The dose ratio between toxic and therapeutic effect is the therapeutic index. An O-nitro compound and/or pharmaceutical composition thereof will preferably exhibit particularly high therapeutic indices in treating disease and disorders characterized by aberrant abnormal cell proliferation. The dosage of an O-nitro compound and/or pharmaceutical composition thereof described herein will preferably be within a range of circulating concentrations that include an effective dose with little or no toxicity.

Combination Therapy

In certain embodiments, 0-nitro compounds and/or pharmaceutical compositions thereof can be used in combination therapy with at least one other therapeutic agent. The O-nitro compound and/or pharmaceutical composition thereof and the therapeutic agent can act additively or, more preferably, synergistically. In some embodiments, an O-nitro compound and/or a pharmaceutical composition thereof is administered concurrently with the administration of another therapeutic agent. In other embodiments, an O-nitro compound and/or pharmaceutical composition thereof is administered prior or subsequent to administration of another therapeutic agent.

In particular, in some embodiments, O-nitro compounds and/or pharmaceutical compositions thereof can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, or triazines)), antimetabolites (e.g., folic acid analogs, pyrimidine analogs (e.g., fluorouracil, floxuridine, cytosine arabinoside, etc.)), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithramycin, mitomycin C, L-asparaginase, interferon alpha), platinum coordination complexes (e.g., cis-platinum, carboplatin, etc.), apoptosis-inducing agents, glutathione-depleting agents or other agents that can alter the redox status of the cell. Those of skill in the art will appreciate that O-nitro compounds may also be used in concurrent combination therapy with both the chemotherapeutic agents listed above and radiotherapy.

Therapeutic Kits

The current invention also provides therapeutic kits comprising O-nitro compounds and/or pharmaceutical compositions thereof. The therapeutic kits may also contain other compounds (e.g., chemotherapeutic agents, natural products, apoptosis-inducing agents, etc.) or pharmaceutical compositions thereof.

Therapeutic kits may have a single container that contains an O-nitro compound and/or pharmaceutical compositions thereof with or without other components (e.g., other compounds or pharmaceutical compositions of these other compounds) or may have a distinct container for each component. In some embodiments, therapeutic kits include an O-nitro compound and/or a pharmaceutical composition thereof packaged for use in combination with the co-administration of a second compound (preferably, a chemotherapeutic agent, a natural product, an apoptosis-inducing agent, etc.) or a pharmaceutical composition thereof. The components of the kit may be pre-complexed or each component may be in a separate distinct container prior to administration to a patient.

The components of the kit may be provided in one or more liquid solutions, such as an aqueous solution or a sterile aqueous solution. The components of the kit may also be provided as solids, which may be converted into liquids by addition of suitable solvents, which may be provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid.

Preferably, a therapeutic kit will contain apparatus (e.g., one or more needles, syringes, eye droppers, pipettes, etc.), which enables administration of the components of the kit.

EXAMPLES

The invention is further defined by reference to the following examples, which describe in detail experiments that, inter alia, demonstrate the effectiveness of O—$NO_2$ compounds in tumor cell therapy. It will be apparent to those skilled in the art that many modifications, both to materials and methods, may be practiced without departing from the scope.

Example 1

Chemosensitization Effect of GLYN in Combination with Cis-Platin on SCC VII Tumor Growth Mice were implanted subcutaneously with a murine squamous cell carcinoma SCC VII tumor cells. When tumors grew to 100-150 $mm^3$ (12 days after implantation), mice with tumors were treated with a single dose of GLYN (100 mg/kg or 300 mg/kg), cis-platin (CDDP, 2 or 5 mg/kg) or in combination. Tumors were measured immediately before treatment and three times a week thereafter.

Figure 2:
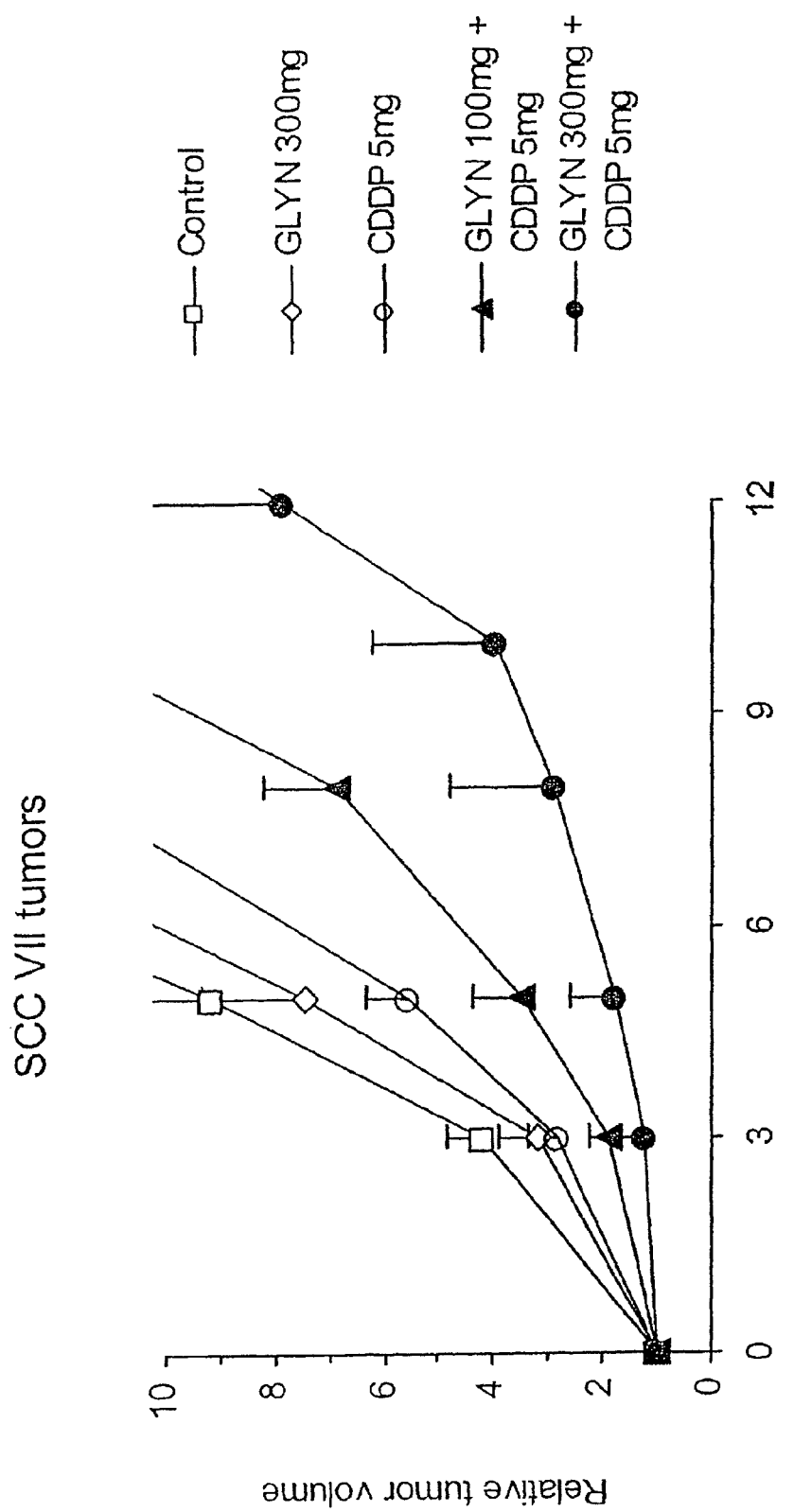
FIG. 2 illustrates the chemosensitization of glycidyl nitrate ("GLYN") in combination with cis-platin on SCC VII tumor growth.

As can be seen in FIG. 2 and Table 1, GLYN at doses of 100 mg/kg or 300 mg/kg significantly enhanced the responses of SCC VII tumors to the treatment with cis-platin. Cis-platin alone at 5 mg/kg inhibited the 4× tumor growth delay time by 1.1 days. When combined with GLYN, the 4× tumor growth delay times increased to 2.8 days and 7.2 days for GLYN 100 mg/kg and 300 mg/kg, respectively, representing a two- to seven-fold increase ($p<0.01$ compared with cis-platin alone). The systemic toxicity indicated by the body weight loss was moderate and mice were recovered one week after treatment (data not shown).

TABLE 1

Comparison of SCC VII tumor growth time in mice treated with GLYN and cis-platin

| | Number of Mice | 4x TGT (day) | TGD (day) | P value (t-test | | |
|---|---|---|---|---|---|---|
| | | | | Control | GLYN | CDDP |
| Control | 5 | 3.0 ± 0.4 | | | | |
| GLYN 300 mg | 5 | 3.6 ± 0.5 | 0.5 ± 0.5 | 0.1 | | |
| CDDP 5 mg | 5 | 4.1 ± 0.4 | 1.1 ± 0.4 | <0.01 | 0.1 | |
| GLYN 100 mg + CDDP 5 mg | 6 | 5.8 ± 0.7 | 2.8 ± 0.7 | <0.01 | <0.01 | <0.01 |
| GLYN 300 mg + CDDP 5 mg | 7 | 10.2 ± 3.1 | 7.2 ± 3.1 | <0.01 | <0.01 | <0.01 |

* 4x TGT (tumor growth time): tumor volume quadrupling time.
** TGD: tumor growth delay time, i.e., 4x TGT of treated tumors minus the mean 4x TGT of control tumors.

Example 2

Radiosensitization Effect of GLYN and SG on SCC VII Tumor Growth

Mice were implanted subcutaneously with SCC VII tumor cells. When tumors reached 100-150 $mm^3$, mice with tumors were treated with a single dose of GLYN (200 mg/kg), sodium glycididazole (SG, 400 mg/kg), 7 Gy radiation, or in combination. Tumors were measured immediately before treatment and three times a week thereafter.

Figure 3:
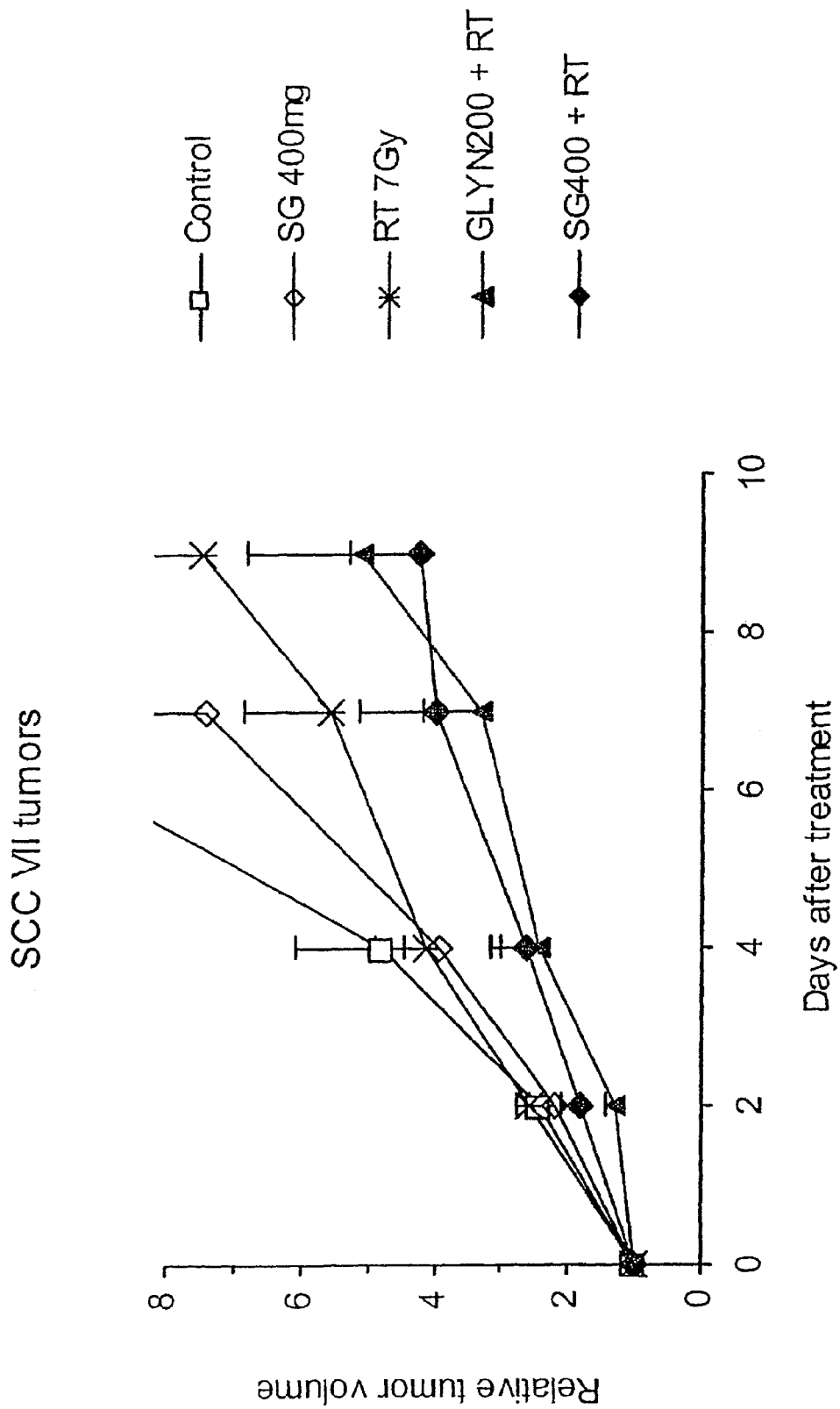
FIG. 3 illustrates radiation sensitization effects of GLYN and SG (sodium glycididazole) in SCC VII tumors.

As shown in FIG. 3, a single dose of 7 Gy radiation (RT7Gy) inhibited the 4× tumor growth by 0.9±1.4 days. The combined therapy of radiation and GLYN or SG inhibited the 4× tumor growth by 4.4 and 3.3 days ($p<0.05$ compared with radiation alone), respectively. There was no statistically significant difference in the 4× tumor growth delay time between the combination therapy of radiation plus GLYN and radiation plus SG ($p=0.2$).

Example 3

Production of Nitric Oxide (NO) in Tumor Cells by GLYN

Figure 4A:
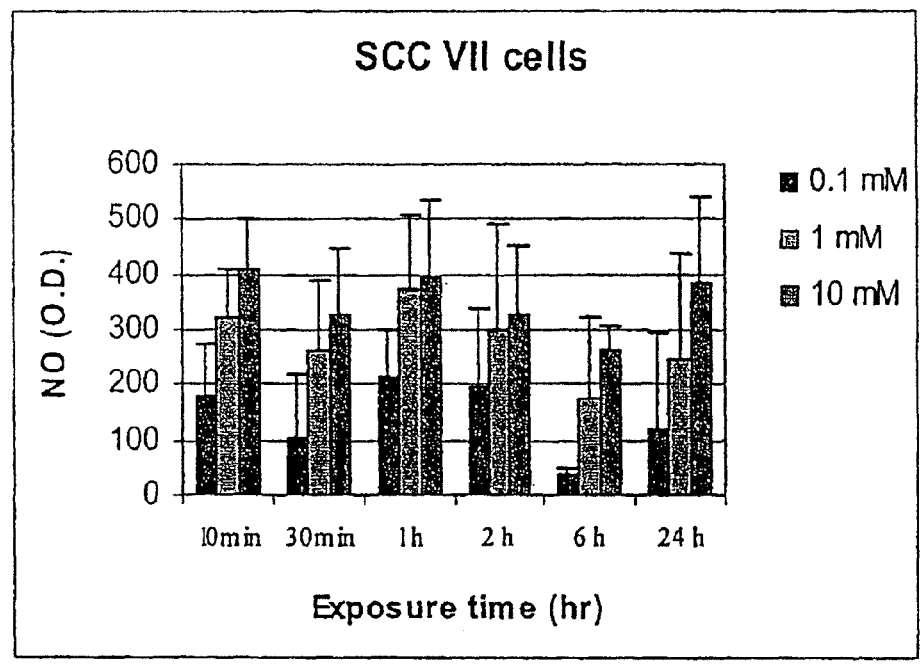
FIG. 4*a* illustrates that nitric oxide generated in tumor cells depended on the dosage of GLYN.
Figure 4B:
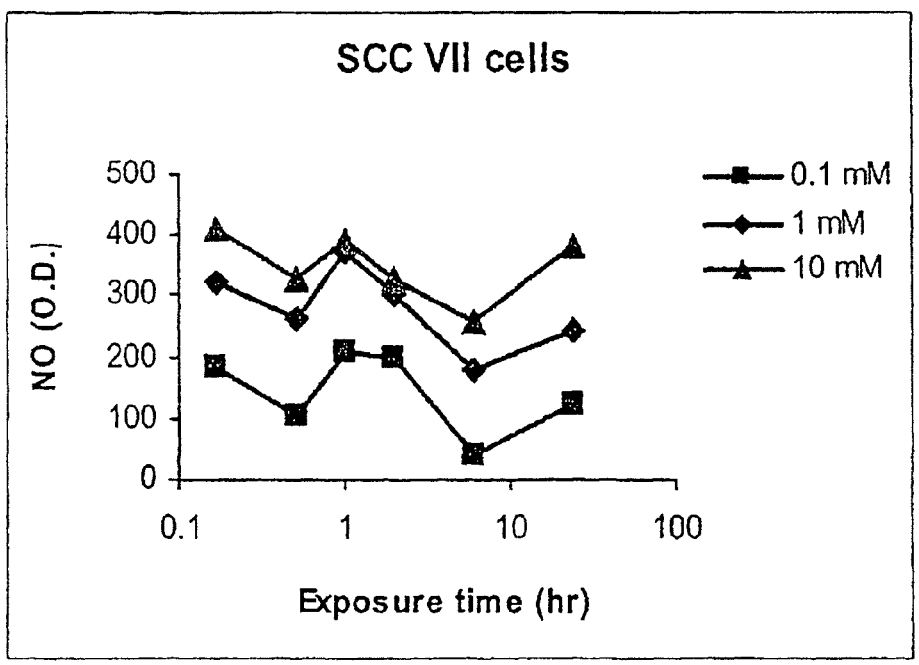
FIG. 4*b* illustrates the nitric oxide concentration in SCC VII cells as a function of time after exposure of SCC VII tumor cells to GLYN.
Figure 5A:
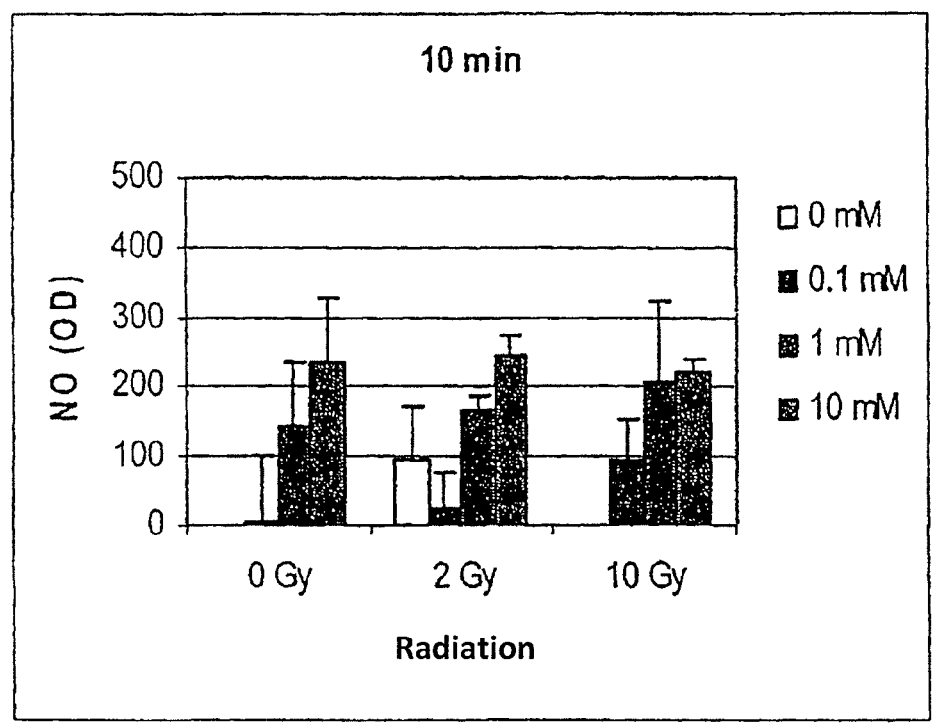
FIGS. 5*a*-5*d* illustrate the concentration of nitric oxide in SCC VII tumor cells after irradiation at ten minutes, one hour, two hours and six hours, respectively.
Figure 5B:
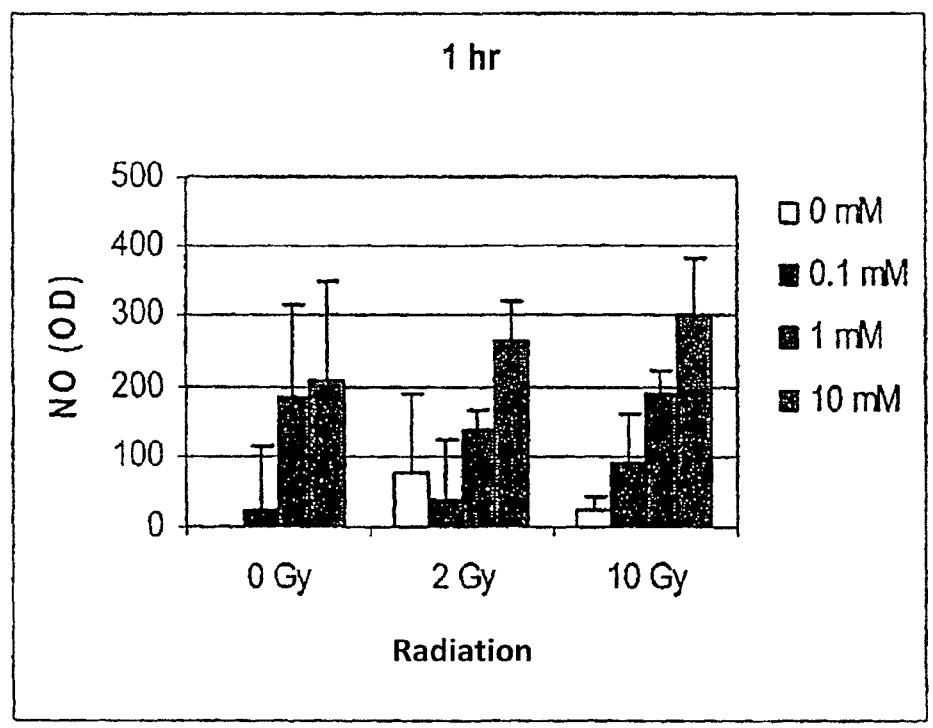
Figure 5C:
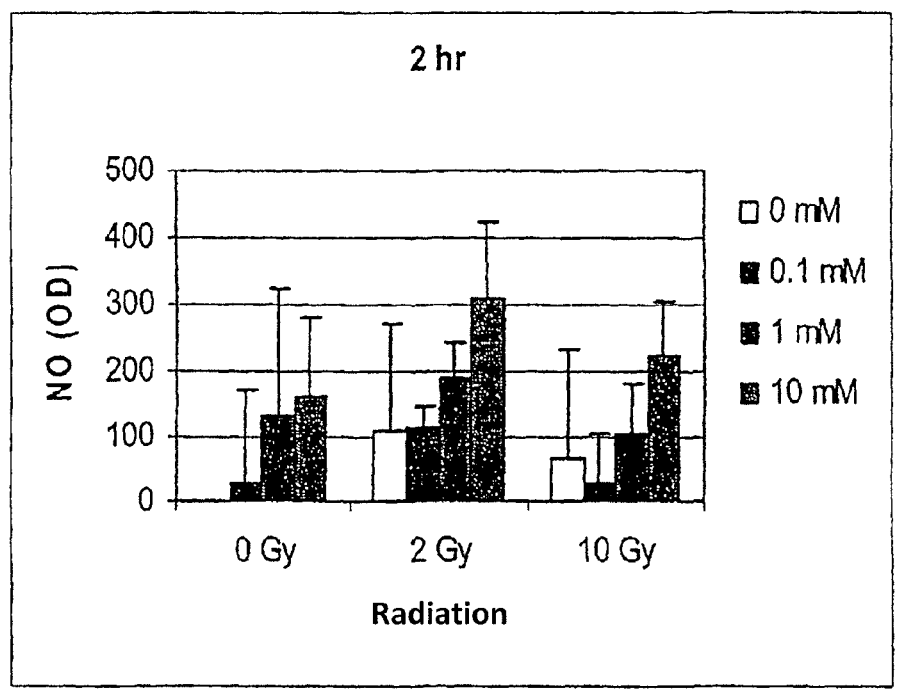
Figure 5D:
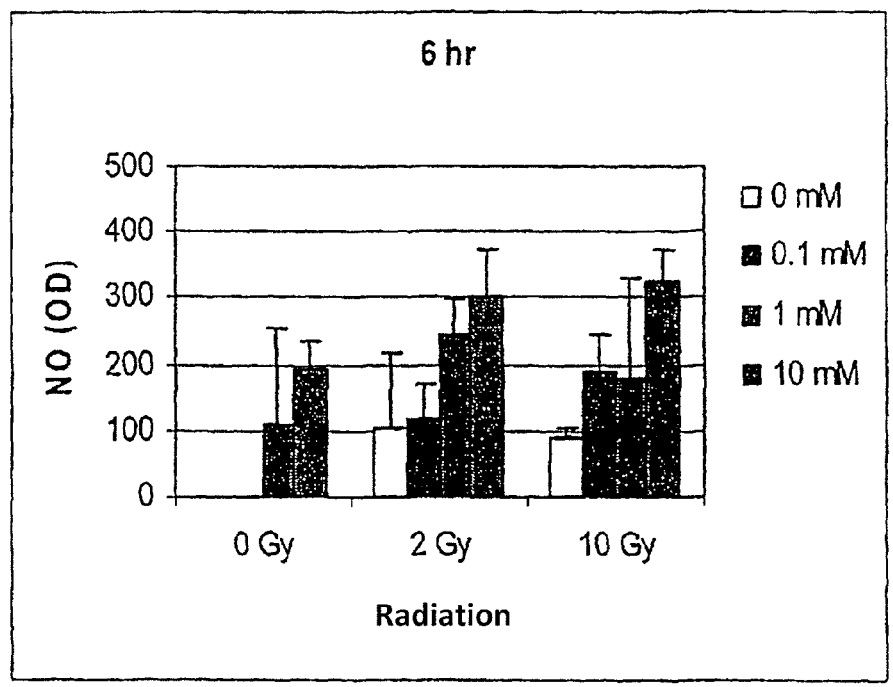

SCC VII tumor cells were grown in 96-well plates overnight at 37° C. A fluorescent probe DAF-FM diacetate was added at a concentration of 10 μM for 1 hour and then washed out. GLYN was added in the growth media at concentrations of 0.1 mM, 1 mM or 10 mM. The green fluorescence was measured at 0 minutes, 10 minutes, 30 minutes, 1 hour, 2 hours, 6 hours and 24 hours after addition of GLYN using a microplate spectrofluorometer with an excitation at 495 nm and an emission at 515 nm (see FIGS. 4a and 4b).

Example 4

Production of Nitric Oxide in Tumor Cells by GLYN and Radiation

SCC VII tumor cells were grown in 96-well plates overnight at 37° C. A fluorescent probe DAF-FM diacetate was added at a concentration of 10 μM for 1 hour and then washed out. GLYN was added in the growth media at concentrations of 0.1 mM, 1 mM or 10 mM. Cells were immediately irradiated with radiation doses of 2 or 10 Gy. The green fluorescence was measured at 0 minutes, 10 minutes, 30 minutes, 1 hour, 2 hours, 6 hours and 24 hours after addition of GLYN using a microplate spectrofluorometer with an excitation at 495 nm and an emission at 515 nm. FIGS. 5a-5d show the production of nitric oxide in SCC VII cells at selected times after exposure to GLYN and radiation. Radiation alone produced a low level of NO in SCC VII tumor cells. When combined with GLYN, the intracellular level of NO slightly increased.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All references, publications and patents cited herein are incorporated by reference in their entirety.

What is claimed is:

1. A pharmaceutical composition comprising glycidyl nitrate or a pharmaceutically acceptable salt, hydrate or solvate thereof, a pharmaceutically acceptable vehicle, and cisplatin.

2. The pharmaceutical composition of claim 1, wherein the pharmaceutical composition comprises a salt of glycidyl nitrate.

3. The pharmaceutical composition of claim 1, wherein the pharmaceutical composition comprises a therapeutically effective amount of glycidyl nitrate or a pharmaceutically acceptable salt, hydrate or solvate thereof.

4. The pharmaceutical composition of claim 1, wherein the pharmaceutical composition comprises from about 0.001 mg to about 100 mg of the glycidyl nitrate or a pharmaceutically acceptable salt, hydrate or solvate thereof per kg body weight.

* * * * *